(12) United States Patent
Juretich et al.

(10) Patent No.: US 11,077,248 B2
(45) Date of Patent: Aug. 3, 2021

(54) MAGNETIC PRESSURE SENSING SYSTEM FOR AN INFUSION PUMP

(71) Applicant: ZEVEX, INC., Salt Lake City, UT (US)

(72) Inventors: Jeffery T. Juretich, Herriman, UT (US); Michael K. Elwood, Farmington, UT (US); Daniel Szczotka, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 734 days.

(21) Appl. No.: 15/745,545

(22) PCT Filed: Jul. 24, 2015

(86) PCT No.: PCT/US2015/041873
§ 371 (c)(1),
(2) Date: Jan. 17, 2018

(87) PCT Pub. No.: WO2017/018974
PCT Pub. Date: Feb. 2, 2017

(65) Prior Publication Data
US 2018/0207360 A1    Jul. 26, 2018

(51) Int. Cl.
*A61M 5/168* (2006.01)
*A61M 5/142* (2006.01)
(Continued)

(52) U.S. Cl.
CPC .... *A61M 5/16854* (2013.01); *A61M 5/14232* (2013.01); *G01R 33/00* (2013.01); *G01R 33/072* (2013.01); *A61M 2005/16863* (2013.01); *A61M 2005/16868* (2013.01); *A61M 2005/16872* (2013.01); *A61M 2205/12* (2013.01); *A61M 2205/3317* (2013.01); *A61M 2205/702* (2013.01)

(58) Field of Classification Search
CPC .......... A61M 5/14232; A61M 5/16854; A61M 2005/16863; A61M 2005/16868; A61M 2005/16872; A61M 2205/12; A61M 2205/3317; A61M 2205/702; A61M 2005/14208; A61M 2205/18; A61M 2205/3331; G01R 33/00; G01R 33/072; A61J 15/0076; A61J 15/0088
See application file for complete search history.

(56) References Cited

U.S. PATENT DOCUMENTS

| 4,758,228 A | | 7/1988 | Williams | |
|---|---|---|---|---|
| 4,936,760 A | * | 6/1990 | Williams | ............... A61M 5/142 417/478 |

(Continued)

FOREIGN PATENT DOCUMENTS

| CN | 102410913 A | 4/2012 |
|---|---|---|
| DE | 19626596 A1 | 1/1997 |

(Continued)

*Primary Examiner* — Brandy S Lee
(74) *Attorney, Agent, or Firm* — Hodgson Russ LLP

(57) ABSTRACT

An infusion pump having one or more magnetic pressure sensors for detecting tubing occlusions is provided with at least one corresponding secondary Hall effect sensor arranged to detect an ambient magnetic field influencing pressure measurements so that corrective action may be taken to mitigate the effects of the ambient magnetic field.

9 Claims, 6 Drawing Sheets

(51) Int. Cl.
*G01R 33/07* (2006.01)
*G01R 33/00* (2006.01)

(56) References Cited

U.S. PATENT DOCUMENTS

| | | | | |
|---|---|---|---|---|
| 4,954,812 A | * | 9/1990 | Lebron | G01R 33/07 |
| | | | | 324/260 |
| 2004/0206916 A1 | * | 10/2004 | Colvin, Jr. | G01N 21/645 |
| | | | | 250/458.1 |
| 2005/0267401 A1 | | 12/2005 | Price et al. | |
| 2013/0238261 A1 | | 9/2013 | Denis et al. | |
| 2014/0326568 A1 | * | 11/2014 | Giessibl | B62M 6/50 |
| | | | | 192/64 |
| 2015/0314066 A1 | | 11/2015 | Shimizu | |

FOREIGN PATENT DOCUMENTS

| | | | |
|---|---|---|---|
| JP | 63275332 A | 11/1988 | |
| JP | H05300896 A | 11/1993 | |
| JP | H0928691 A | 2/1997 | |
| JP | 2014219387 A | 11/2014 | |

* cited by examiner

MAGNETIC PRESSURE SENSING SYSTEM FOR AN INFUSION PUMP

FIELD OF THE INVENTION

The present invention relates generally to infusion pumps for controlled delivery of liquid food and medications to patients. More specifically, the present invention relates to a magnetic system for measuring fluid pressure within tubing of an administration set connected to an infusion pump.

BACKGROUND OF THE INVENTION

Programmable infusion pumps are used to carry out controlled delivery of liquid food for enteral feeding and medications for various purposes, for example pain management. In a common arrangement, an infusion pump receives a disposable administration set comprising a cassette removably received by the pump and flexible tubing connected to the cassette for providing a fluid delivery path through the pump.

The administration set may include a pumping segment of tubing that wraps around a rotor mechanism of the pump, and the cassette may include a pair of tubing connectors to which opposite ends of the tubing segment are connected. The rotor mechanism may have pinch rollers or fingers that deform the tubing segment as the rotor rotates to progressively urge fluid through the tubing in a peristaltic manner. The cassette may have another pair of tubing connectors for connecting inflow tubing carrying fluid from a fluid source and outflow tubing leading to a patient. As a result, a flow path is provided from the inflow tubing, through the tubing segment, to the outflow tubing.

Infusion pumps of the type described above may include one or more pressure sensors arranged to measure fluid pressure within the tubing of the administration set. Pressure sensing is an important safety feature because an unexpected variation in fluid pressure may indicate an unsafe condition, such as an occlusion within the tubing that is blocking delivery of food or medication to the patient. In a common arrangement, a pump may have an upstream pressure sensor situated upstream from the pumping mechanism (e.g. the peristaltic rotor) and a downstream pressure sensor situated downstream from the pumping mechanism. If an occlusion occurs at a location upstream from the pressure sensor, a vacuum condition is created and causes contraction of the tubing at the sensor location. Conversely, if an occlusion occurs at a location downstream from the pressure sensor, fluid pressure builds and causes expansion of the tubing at the sensor location. Various types of pressure sensors are known for measuring pressure by detecting contraction and expansion of the tubing using a variety of transducer technologies, including optical, magnetic, ultrasonic, and load cell transducers.

With specific regard to magnetic pressure sensors, it is known to provide a magnet arranged to move in response to contraction and expansion of the tubing, and a corresponding Hall effect sensor arranged to generate an output voltage signal proportional to the strength of the magnetic field of the magnet. As the magnet moves closer to the Hall effect sensor, the voltage signal increases, and as the magnet moves away from the Hall effect sensor, the voltage signal decreases. Magnetic pressure sensors of the type described above are economical to manufacture and incorporate into an infusion pump. However, such magnetic sensors are susceptible to inaccuracy when the pump is in close proximity to an ambient magnetic field unrelated to the intended magnetic field of the pressure sensor magnet. For example, if the infusion pump is discretely carried in the user's backpack or purse, it may come into close proximity with a magnetic toy or magnetic purse latch. There is also the possibility that the pump will be used near an ambient magnetic field source in a hospital or home environment. Inaccurate measurements may lead to false occlusion alarms that are disruptive to the patient's infusion protocol and medical staff. Inaccurate pressure measurements may also result in a missed occlusion alarm when an occlusion is actually present, a situation that may have serious safety consequences for the patient.

What is needed is a magnetic pressure sensor system for an infusion pump that accounts for the possibility of an unintended ambient magnetic field that may influence pressure measurements.

SUMMARY OF THE INVENTION

An infusion pump operable to pump fluid through tubing connected to the infusion pump and having one or more magnetic pressure sensors for detecting tubing occlusions is provided with at least one secondary Hall effect sensor arranged to detect an ambient magnetic field influencing pressure measurements so that corrective action may be taken to mitigate the effects of the ambient magnetic field.

The invention may be embodied by an infusion pump comprising at least one pressure sensor for measuring fluid pressure within the tubing, wherein the pressure sensor includes a magnet arranged to move in response to radial contraction and expansion of the tubing and a corresponding primary Hall effect sensor measuring magnetic field strength, and further comprising at least one secondary Hall effect sensor arranged to detect an ambient magnetic field in the vicinity of the infusion pump capable of being detected by the primary Hall effect sensor.

In a specific embodiment, an infusion pump having an upstream magnetic pressure sensor and a downstream magnetic pressure sensor is provided with a pair of corresponding secondary Hall effect sensors located near the upstream and downstream pressure sensors, respectively.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
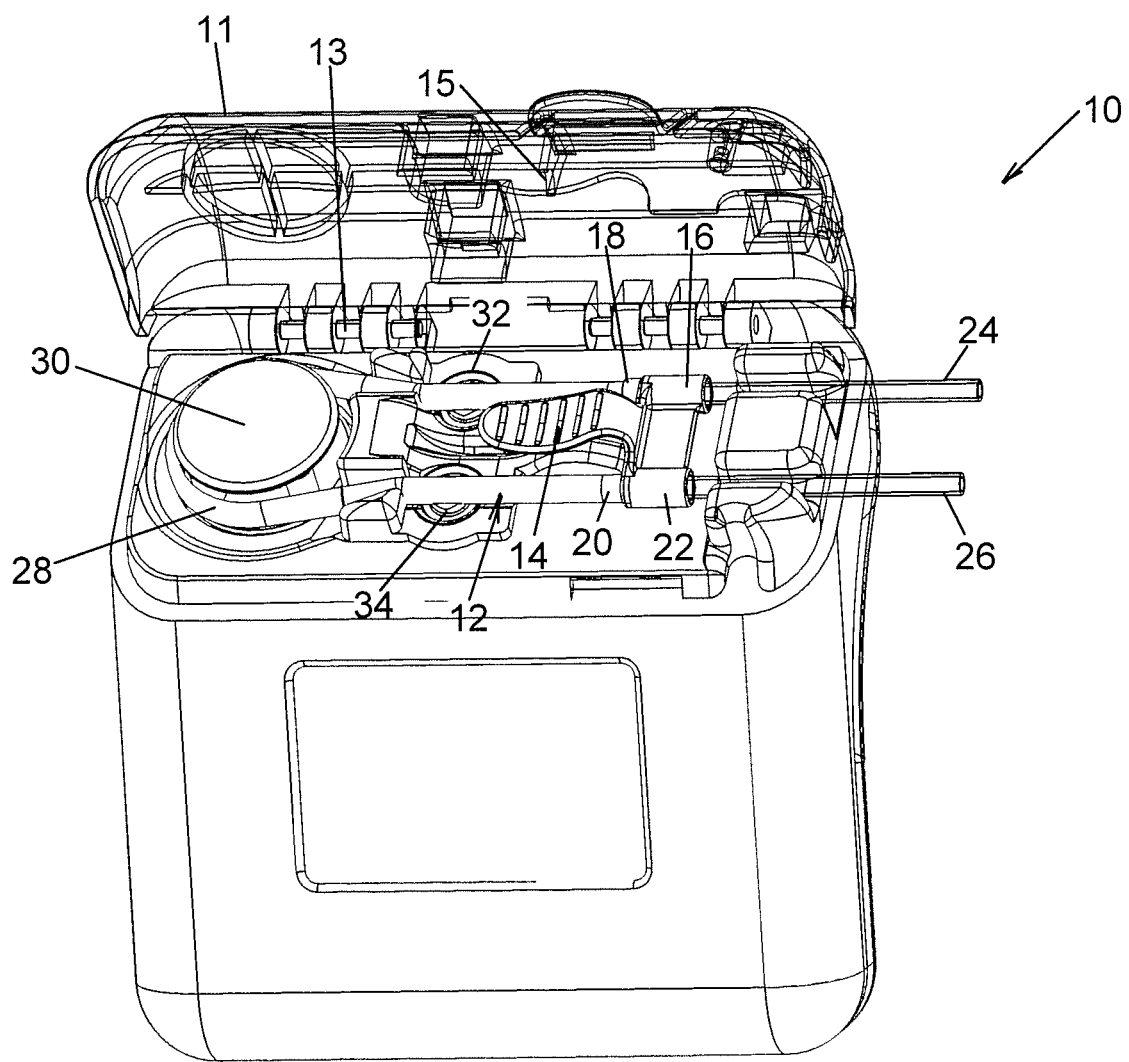
FIG. 1 is a perspective view of an infusion pump formed in accordance with an embodiment of the present invention, wherein an administration set is shown installed in the pump.

FIG. 1 shows an infusion pump 10 having a door 11 connected to pump 10 by a hinge 13 on one side of the door and a releasable latch 15 on the other side of the door. An administration set 12 is removably received in pump 10. Administration set 12 includes a cassette 14 having an inflow connector 16, an upstream pumping segment connector 18 in flow communication with inflow connector 16, a downstream pumping segment connector 20, and an outflow connector 22 in flow communication with downstream pumping segment connector 20. Administration set 12 may further include inflow tubing 24 having one end mated to inflow connector 16 and an opposite end (not shown) connected to a fluid source, and outflow tubing 26 having one end connected to outflow connector 22 and an opposite end (not shown) connected to a patient. Finally, administration set 14 may further include a pumping segment of tubing 28 having one end mated to upstream pumping segment connector 18 and an opposite end mated to downstream pumping segment connector 20.

In the illustrated embodiment, pump 10 is a rotary peristaltic pump having a motor-driven rotor 30 acting as a pumping mechanism, wherein pumping segment 28 is wrapped around rotor 30 and is engaged by angularly spaced rollers on rotor 30 as the rotor rotates to provide peristaltic pumping action forcing liquid through the tubing of administration set 12. As may be understood by reference to FIG. 1, when rotor 30 rotates in a counter-clockwise direction, liquid is moved from inflow tubing 24 through inflow connector 16 and upstream pumping segment connector 18 to pumping segment 28, and then from pumping segment 28 through downstream pumping segment connector 20 and outflow connector 22 to outflow tubing 26. Although the present invention is described in the context of a rotary peristaltic pump having a rotor pumping mechanism, the invention is not limited to this type of infusion pump.

Figure 2:
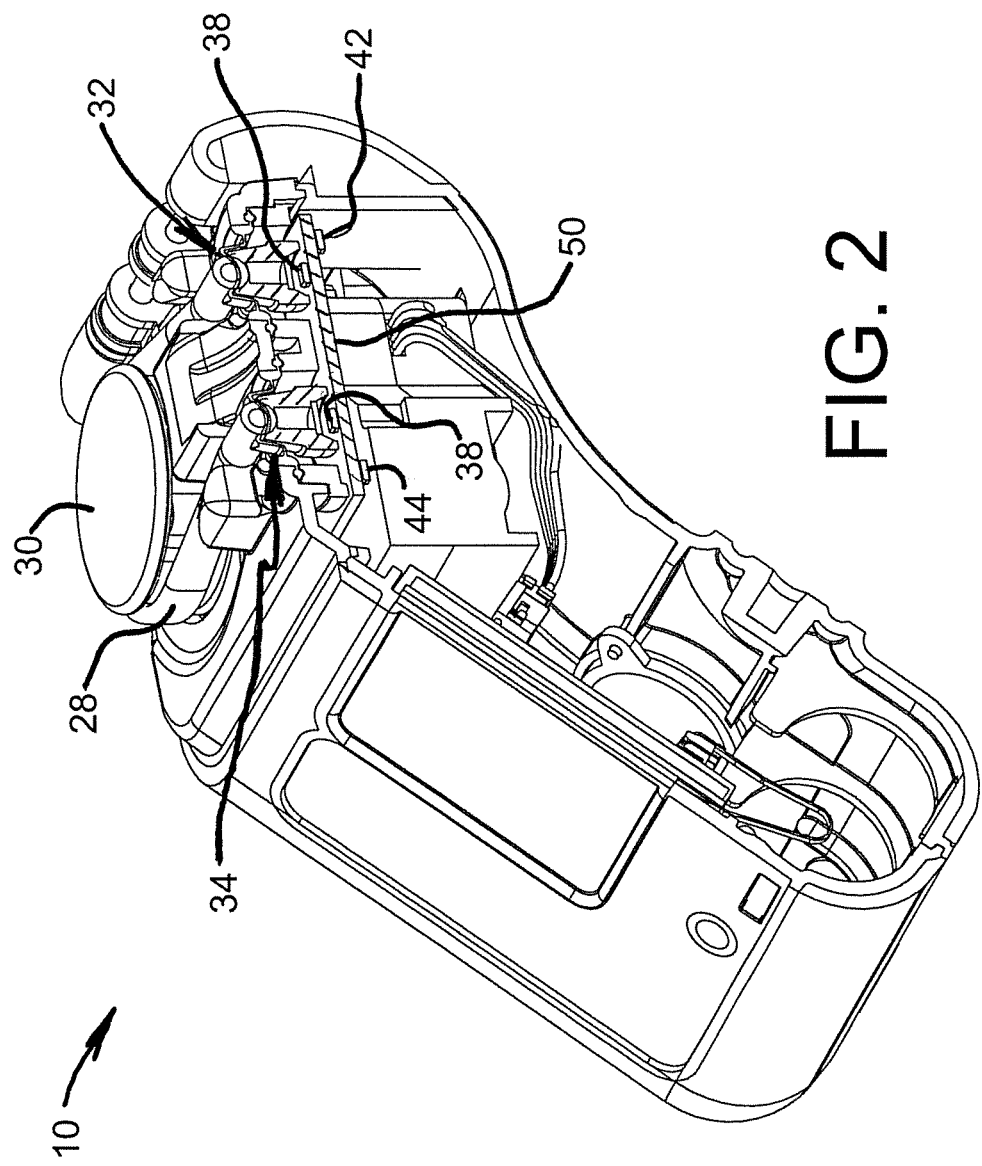
FIG. 2 is a cross-sectioned perspective view of the infusion pump shown in FIG. 1, wherein a door of the pump is omitted and the cross-sectional plane extends transversely across upstream and downstream pressure sensors of the pump.
Figure 3:
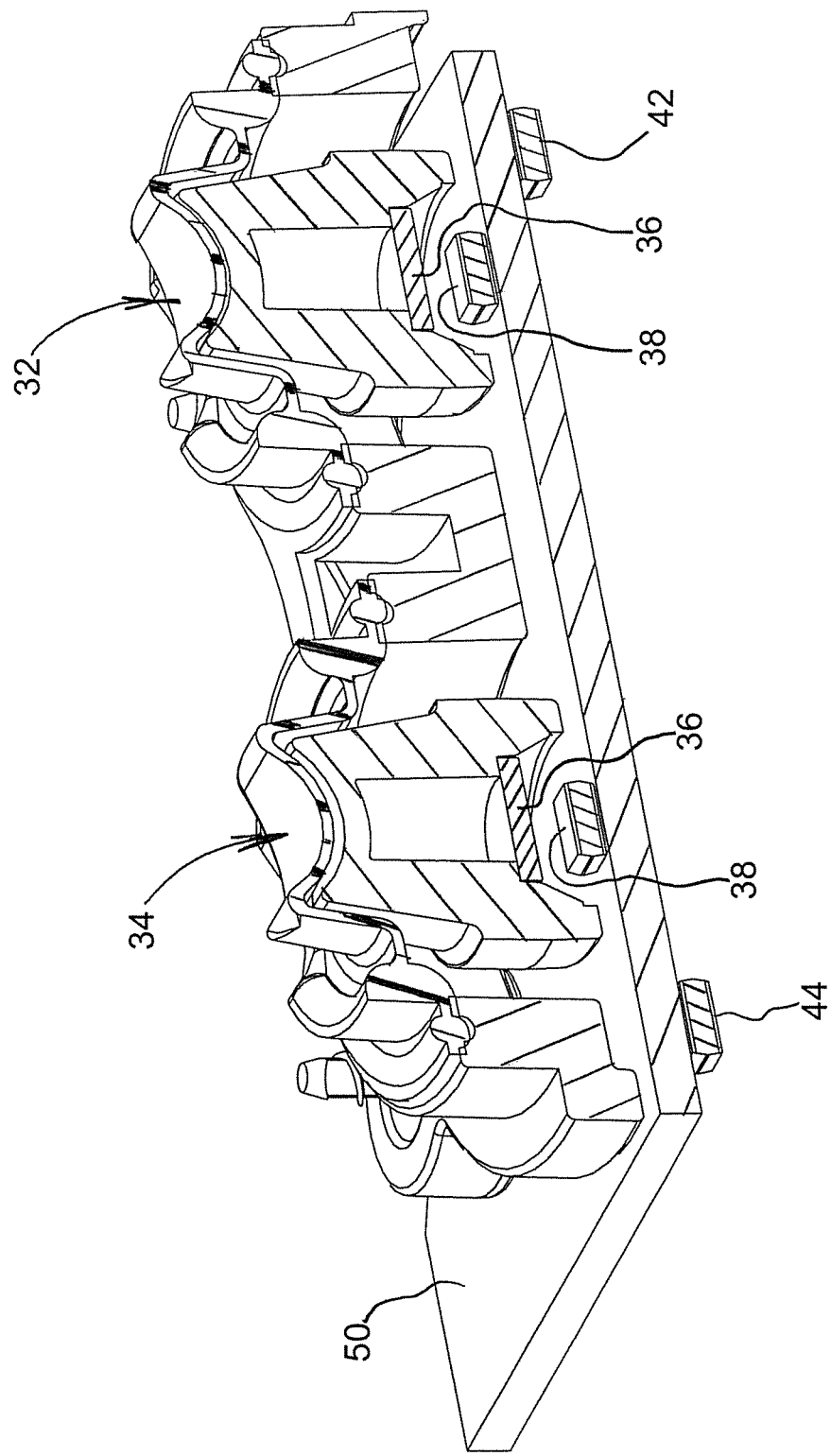
FIG. 3 is an enlarged cross-sectioned perspective view of the upstream and downstream pressure sensors of the pump and a printed circuit board associated therewith.
Figure 4:
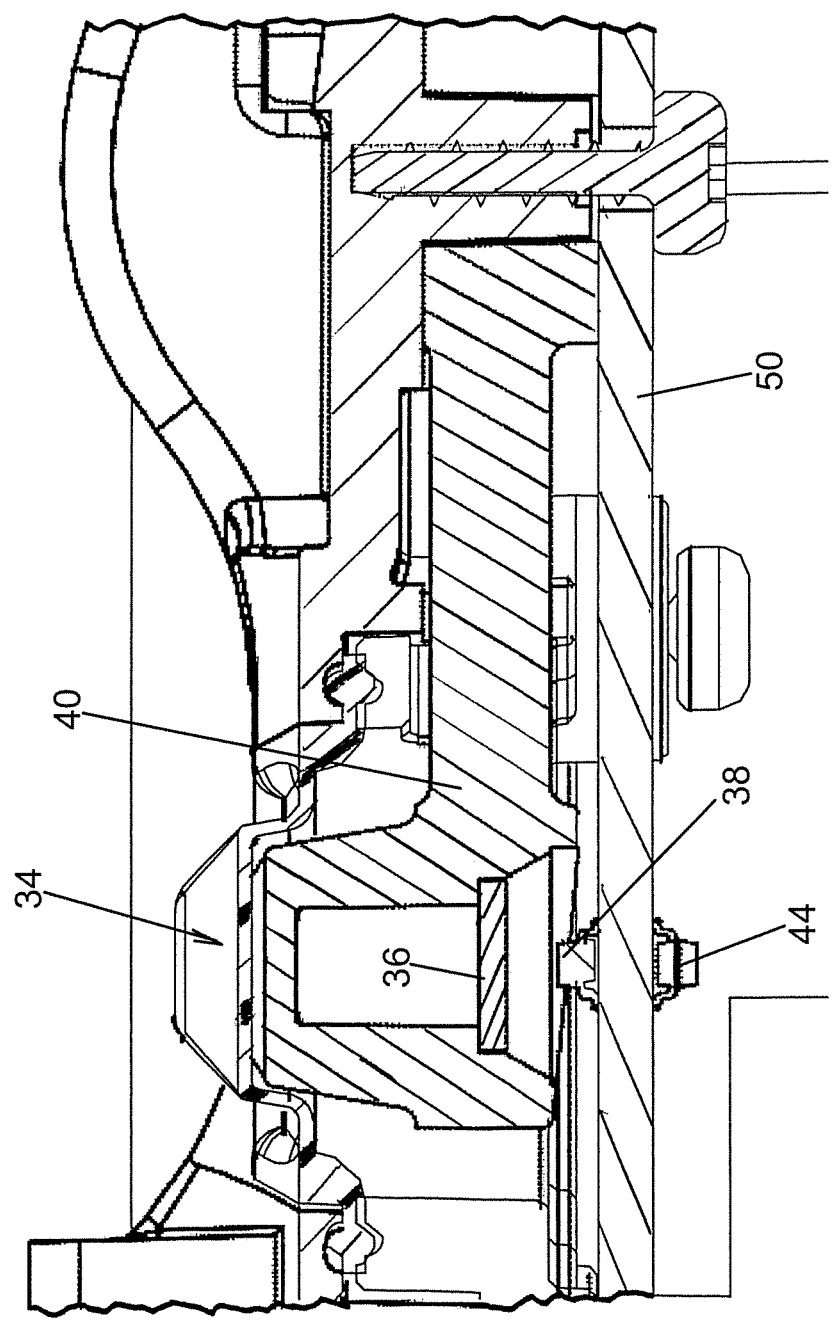
FIG. 4 is a detailed cross-sectional view through a downstream pressure sensor of the pump, wherein the cross-sectional plane extends longitudinally through the downstream pressure sensor.

As best seen in FIGS. 2-4, infusion pump 10 comprises an upstream pressure sensor 32 and a downstream pressure sensor 34. Upstream pressure sensor 32 is arranged upstream from the pumping mechanism (e.g. rotor 30) for measuring fluid pressure within the pumping segment of tubing 28 at a location between upstream pumping segment connector 18 and rotor 30. Downstream pressure sensor 34 is arranged downstream from the rotor 30 for measuring fluid pressure within the tubing segment 28 at a location between rotor 30 and downstream pumping segment connector 20. Pressure sensors 32 and 34 are magnetic pressure sensors and may have a similar construction illustrated in detail in FIGS. 3 and 4. Each pressure sensor 32, 34 may include a permanent magnet 36 having an intended magnetic field and a primary Hall effect sensor 38, wherein the magnet 36 is arranged to move relative to the primary Hall effect sensor 38 in response to radial contraction and expansion of tubing segment 28. For example, magnet 36 may be spring-biased to maintain responsive connection with an outer wall surface of tubing segment 28 such that as tubing segment 28 radially contracts, magnet 36 moves upward in FIGS. 3 and 4 away from primary Hall effect sensor 38, and as tubing segment 28 radially expands, magnet 36 moves downward in FIGS. 3 and 4 toward primary Hall effect sensor 38. As seen in FIG. 4, magnet 36 may be supported by a cantilevered spring member 40 to provide the mentioned biasing. Those skilled in the art will recognize that other configurations for biasing magnet 36 may be used, for example a coil spring and plunger configuration, without straying from the present invention.

As may be understood, primary Hall effect sensor 38 generates an output voltage signal proportional to the magnetic field strength it detects. When there are no ambient magnetic fields present and detectable by primary Hall effect sensor 38, such that primary Hall effect sensor 38 only detects the intended magnetic field associated with magnet 36, the primary output signal generated by primary Hall effect sensor 38 represents fluid pressure in tubing segment 28.

In accordance with the present invention, infusion pump 10 may comprise a secondary Hall effect sensor 42 associated with upstream pressure sensor 32 and another secondary Hall effect sensor 44 associated with downstream pressure sensor 34. Secondary Hall effect sensor 42 is arranged near primary Hall effect sensor 38 of upstream pressure sensor 32 to detect ambient magnetic fields in the vicinity of the infusion pump 10 capable of being detected by such primary Hall effect sensor 38. Secondary Hall effect sensor 42 generates a secondary output voltage signal proportional to magnetic field strength that it detects. Secondary Hall effect sensor 42 has a nominal output signal value that corresponds to pressure equilibrium between the interior and exterior of tubing segment 28 and is caused solely by the sensor's detection of the intended magnetic field of magnet 36 (i.e. no ambient magnetic fields are detected). The output signal generated by secondary Hall effect sensor 42 may also have a known fluctuation range about the nominal value corresponding to travel limits of magnet 36 in the absence of ambient magnetic fields. The nominal output signal value and fluctuation range may be determined during calibration of infusion pump 10 and stored in memory. Similarly, a nominal output signal value and fluctuation range may also be determined for the primary Hall effect sensor 38. Based on the calibration information, an expected behavior of the secondary output signal in the absence of ambient magnetic fields may be determined and stored in the pump memory as a reference. Thus, by comparing a sampled value of the secondary output signal from Hall effect sensor 42 to its expected value, the presence of an ambient magnetic field influencing the primary output signal of Hall effect sensor 38 in upstream pressure sensor 32 may be detected. In similar fashion, the other secondary Hall effect sensor 44 associated with downstream pressure sensor 34 provides an output signal that serves as a basis for determining the presence of an ambient magnetic field influencing the primary output signal of Hall effect sensor 38 in downstream pressure sensor 34.

In an embodiment of the invention, the two primary Hall effect sensors 38, 38 and the two secondary Hall effect sensors 42, 44 may be arranged on the same printed circuit board 50. FIG. 3 illustrates a possible locational arrangement of the various Hall effect sensors. As may be seen, upstream pressure sensor 32 is on the side of pump 10 near door hinge 13, and the associated primary Hall effect sensor 38 is mounted on a top side of PCB 50 directly under magnet 36 of upstream pressure sensor 32. The corresponding secondary Hall effect sensor 42 may be mounted on PCB 50 closer to hinge 13 for detecting ambient fields originating outside the pump housing. As shown in the illustrated embodiment, secondary Hall effect sensor 42 may be mounted on a bottom side of PCB 50 adjacent a side edge of the PCB closest to hinge 13. Downstream pressure sensor 34 is on the opposite side of pump 10 near door latch 15.

Thus, a mirror image mounting arrangement of primary Hall effect sensor 38 of downstream pressure sensor 34 and corresponding secondary Hall effect sensor 44 on PCB 50 may be used as shown in FIG. 3.

Figure 5:
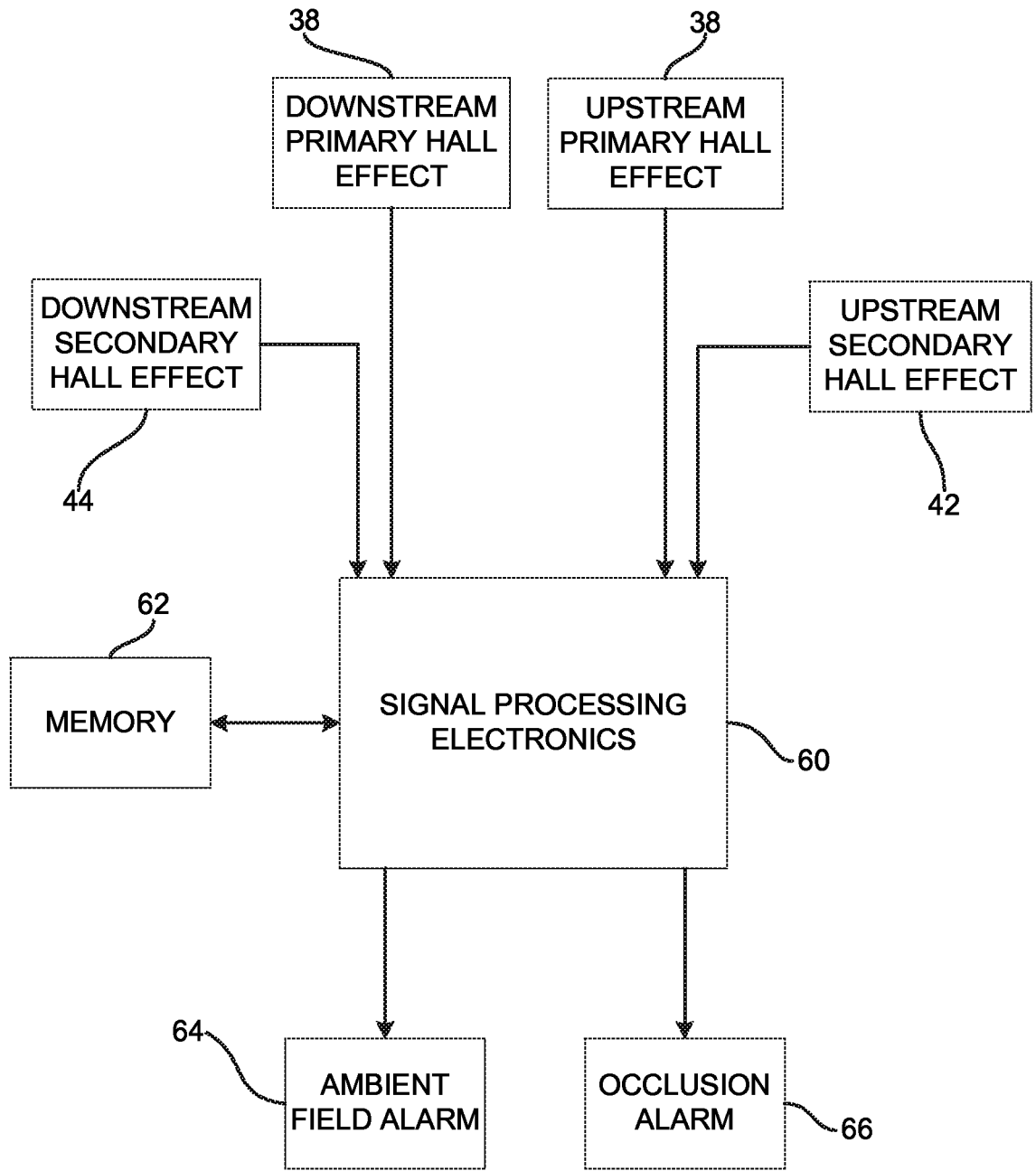
FIG. 5 is a schematic block diagram showing electronic circuitry associated with a pressure sensing system of the infusion pump shown in FIGS. 1 and 2.
Figure 6:
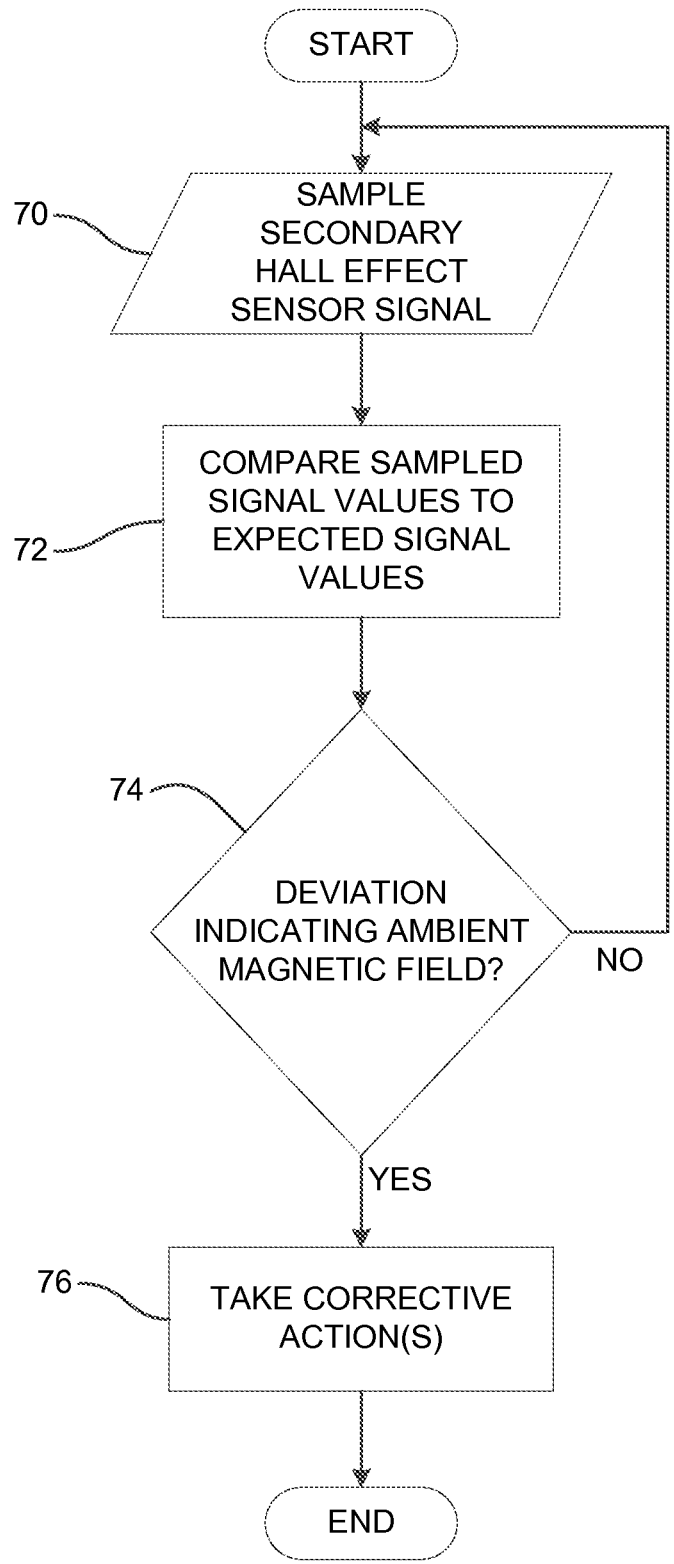
FIG. 6 is a flow diagram illustrating a method according to another embodiment of the present invention.

FIG. 5 is a schematic block diagram showing electronic circuitry associated with a pressure sensing system embodying the present invention. Signal processing electronics 60 may include analog-to-digital conversion circuitry for converting the analog voltage signals generated by primary Hall effect sensors 38, 38 and secondary Hall effect sensors 42, 44 into digital form. Signal processing electronics 60 may further include a programmed microprocessor executing stored instructions causing the microprocessor to compare the digitized output signals from secondary Hall effect sensors 42, 44 to expected signal values stored in memory 62 during pump calibration, and to take one or more corrective actions based on whether the comparison indicates the presence of an ambient magnetic field. In this regard, reference is made to FIG. 6 for a general illustration of programming logic that may be executed by signal processing electronics 60. In step 70, the secondary output signals from secondary Hall effect sensors 42 and 44 are sampled. In step 72, the sampled secondary signal values are compared to expected signal values. Decision block 74 branches flow based on whether a deviation of the sampled signal value to the expected signal value indicates an ambient magnetic field is present. If not, flow returns to step 70. If an ambient magnetic field is found in decision block 74, flow proceeds to step 76, whereby one or more corrective actions are taken. The corrective actions may be programmed steps executed by signal processing electronics 60, or steps taken by a pump operator.

One possible corrective action is to adjust a calculation of the fluid pressure based on the secondary output signal. For example, if secondary Hall effect sensor 44 associated with downstream pressure sensor 34 detects an ambient magnetic field, the primary output signal generated by corresponding primary Hall effect sensor 38 of downstream pressure sensor 34 may be adjusted to compensate for the detected ambient magnetic field. In other words, the primary output signal may be adjusted to a corrected value that solely reflects the contribution of magnet 36 and eliminates influence from the ambient magnetic field. In this way, the pressure correlated to the primary output signal will accurately reflect the fluid pressure in tubing segment 28 that is being measured.

Another possible corrective action is to trigger an ambient field alarm 64 to indicate presence of the ambient magnetic field to a pump operator. The pump operator may then take further corrective action by removing the infusion pump from the ambient magnetic field by determining the source of the ambient magnetic field and either moving the pump away from the source or moving the source away from the pump.

Since pump 10 already includes an occlusion alarm 66 triggered when either pressure sensor 32, 34 detects an occlusion, the same alarm 66 may be triggered when an ambient magnetic field is detected, but in a different manner communicating to the operator that an ambient magnetic field is present rather than an occlusion.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the invention.

What is claimed is:

1. An infusion pump operable to pump fluid through tubing connected to the infusion pump, wherein the infusion pump comprises:
    at least one pressure sensor for measuring fluid pressure within the tubing, wherein the pressure sensor includes a magnet having an intended magnetic field and a primary Hall effect sensor, wherein the magnet is arranged to move relative to the primary Hall effect sensor in response to radial contraction and expansion of the tubing and the primary Hall effect sensor generates a primary output signal proportional to magnetic field strength detected thereby, the primary output signal representing fluid pressure in the tubing when the primary Hall effect sensor solely detects the intended magnetic field;
    at least one secondary Hall effect sensor arranged to detect an ambient magnetic field in the vicinity of the infusion pump capable of being detected by the primary Hall effect sensor, wherein the secondary Hall effect sensor generates a secondary output signal proportional to magnetic field strength detected thereby; and
    a memory storing an expected output signal value and an expected output signal fluctuation range of the at least one secondary Hall effect sensor generated in response to the intended magnetic field of the magnet and in the absence of the ambient magnetic field, wherein the expected output signal value corresponds to a position of the magnet at pressure equilibrium between an interior and an exterior of the tubing and the expected output signal fluctuation range represents travel limits of the magnet associated with radial contraction and expansion of the tubing;
    whereby presence of the ambient magnetic field is determined based on comparison of the secondary output signal to the expected output signal value.

2. The infusion pump according to claim 1, further comprising a pumping mechanism for engaging the tubing to cause fluid flow in a flow direction through the tubing, wherein the at least one pressure sensor comprises an upstream pressure sensor located upstream from the pumping mechanism and a downstream pressure sensor located downstream from the pumping mechanism.

3. The infusion pump according to claim 2, wherein the at least one secondary Hall effect sensor comprises an upstream secondary Hall effect sensor associated with the upstream pressure sensor and a downstream secondary Hall effect sensor associated with the downstream pressure sensor.

4. The infusion pump according to claim 3, further comprising a printed circuit board, wherein the primary Hall effect sensor of the upstream pressure sensor, the primary Hall effect sensor of the downstream pressure sensor, the upstream secondary Hall effect sensor, and the downstream secondary Hall effect sensor are mounted on the printed circuit board.

5. The infusion pump according to claim 4, wherein the printed circuit board has first and second opposite sides, the primary Hall effect sensor of the upstream pressure sensor and the primary Hall effect sensor of the downstream pressure sensor are mounted on the first side of the printed circuit board, and the upstream secondary Hall effect sensor and the downstream secondary Hall effect sensor are mounted on the second side of the printed circuit board.

6. A method of improving safety in an infusion pump having a pressure sensor for measuring fluid pressure within a length of tubing, wherein the pressure sensor includes a magnet having an intended magnetic field and a primary Hall effect sensor, wherein the magnet is arranged to move relative to the primary Hall effect sensor in response to radial contraction and expansion of the tubing and the primary Hall effect sensor generates a primary output signal proportional to magnetic field strength detected thereby, the primary output signal representing fluid pressure in the tubing when the primary Hall effect sensor solely detects the intended magnetic field, the method comprising the steps of:

A) providing a secondary Hall effect sensor to detect ambient magnetic fields capable of being detected by the primary Hall effect sensor, wherein the secondary Hall effect sensor generates a secondary output signal proportional to magnetic field strength detected thereby;

B) providing a memory storing an expected output signal value and an expected output signal fluctuation range of the at least one secondary Hall effect sensor generated in response to the intended magnetic field of the magnet and in the absence of an ambient magnetic field, wherein the expected output signal value corresponds to a position of the magnet at pressure equilibrium between an interior and an exterior of the tubing and the expected output signal fluctuation range represents travel limits of the magnet associated with radial contraction and expansion of the tubing;

C) comparing the secondary output signal to the expected output signal value to determine presence of the ambient magnetic field; and D) taking a corrective action in response to the determination.

7. The method according to claim 6, wherein the corrective action includes adjusting a calculation of the fluid pressure based on the secondary output signal.

8. The method according to claim 6, wherein the corrective action includes triggering an alarm to indicate presence of the ambient magnetic field.

9. The method according to claim 6, wherein the corrective action includes removing the infusion pump from the ambient magnetic field.

* * * * *